US012740711B2

(12) United States Patent
Presura et al.

(10) Patent No.: US 12,740,711 B2
(45) Date of Patent: Sep. 22, 2026

(54) DETECTING DISTANCE OF A PROBE TO PULP OF A TOOTH

(71) Applicant: KONINKLIJKE PHILIPS N.V., Eindhoven (NL)

(72) Inventors: Cristian Nicolae Presura, Veldhoven (NL); Jindrich Charvat, Statenice (CZ); Martin Pekar, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 266 days.

(21) Appl. No.: 18/267,933

(22) PCT Filed: Dec. 13, 2021

(86) PCT No.: PCT/EP2021/085340
§ 371 (c)(1),
(2) Date: Jun. 16, 2023

(87) PCT Pub. No.: WO2022/128831
PCT Pub. Date: Jun. 23, 2022

(65) Prior Publication Data

US 2024/0008747 A1 Jan. 11, 2024

(30) Foreign Application Priority Data

Dec. 16, 2020 (EP) .................................... 20214511

(51) Int. Cl.
*A61B 5/00* (2006.01)
*A61C 1/08* (2006.01)
*A61C 19/04* (2006.01)

(52) U.S. Cl.
CPC .......... *A61B 5/0088* (2013.01); *A61B 5/0075* (2013.01); *A61B 5/682* (2013.01);
(Continued)

(58) Field of Classification Search
CPC ..... A61B 5/0088; A61B 5/0075; A61B 5/682; A61B 5/6844; A61C 1/082; A61C 19/04
See application file for complete search history.

(56) References Cited

U.S. PATENT DOCUMENTS 5,725,480 A * 3/1998 Oosta .................... A61B 5/442
600/556
5,818,587 A 10/1998 Devaraj et al.
(Continued)

FOREIGN PATENT DOCUMENTS

CN 110559091 A 12/2019
JP 2013233303 A 11/2013
(Continued)

OTHER PUBLICATIONS

International Search Report and Written Opinion Dated Apr. 5, 2022 For International Application No. PPCT/EP2021/085340 Filed Dec. 13, 2021.

(Continued)

*Primary Examiner* — Baisakhi Roy

(57) ABSTRACT

A method and an apparatus for detecting distance of a probe contacting a tooth surface to pulp of a tooth by determining an indication of thickness of dentine of the tooth is provided. The method comprises illuminating the dental tissue of the tooth with a probe, then receiving the data representing scattered light from the dental tissue. A spectra of the scattered light is then obtained and analyzed to further obtain a spectral analysis re-suit. An indication of the thickness of the dentine of the tooth is then determined based on the spectral analysis result. The method may help to prevent the unintended exposure of pulp during dental treatments such as drilling.

7 Claims, 9 Drawing Sheets

(52) U.S. Cl.
CPC ............ *A61B 5/6844* (2013.01); *A61C 1/082* (2013.01); *A61C 19/04* (2013.01)

(56) References Cited

U.S. PATENT DOCUMENTS

| | | | | |
|---|---|---|---|---|
| 6,957,099 | B1 * | 10/2005 | Arnone | G01N 21/3586 600/473 |
| 2001/0049082 | A1 * | 12/2001 | Kerschbaumer | A61C 19/10 356/408 |
| 2005/0100866 | A1 * | 5/2005 | Arnone | A61B 5/417 433/29 |
| 2007/0021670 | A1 * | 1/2007 | Mandelis | A61B 5/0088 600/473 |
| 2008/0024788 | A1 * | 1/2008 | Shimizu | G01B 9/02091 356/497 |
| 2009/0087811 | A1 * | 4/2009 | Ertl | A61B 5/0088 433/29 |
| 2009/0155735 | A1 | 6/2009 | Hauger | |
| 2011/0102566 | A1 * | 5/2011 | Zakian | A61B 5/0086 348/66 |
| 2012/0200687 | A1 * | 8/2012 | Kikuchi | A61B 1/0653 348/370 |
| 2012/0271176 | A1 * | 10/2012 | Moghaddam | A61B 5/489 600/476 |
| 2019/0110689 | A1 * | 4/2019 | Ertl | A61B 5/682 |
| 2019/0269485 | A1 * | 9/2019 | Elbaz | A61B 5/1079 |
| 2020/0015923 | A1 | 1/2020 | Scheib et al. | |

FOREIGN PATENT DOCUMENTS

| | | |
|---|---|---|
| WO | 2007072592 A1 | 6/2007 |
| WO | 2017045773 A1 | 3/2017 |

OTHER PUBLICATIONS http://www.confidentabc.com/ Real time feedback with ConfiDent—Specially designed for the accurate placement of dental implants. copyright 2021 @ ConfiDent ABC.

Bjorndal et al; "Management of deep caries and the exposed pulp" First published: Apr. 15, 2019 International Endodontic Journal, 52, 949-973, 2019. https://doi.org/10.1111/iej.13128 https://onlinelibrary.wiley.com/doi/pdfdirect/10.1111/iej.13128.

Bakland, Leif K.; "Dental trauma guidelines"; Pediatric Dentistry, 2013; 35(2), 106-108.

Bhaskar et al; "Dental vitality tests and pulp status"; Journal of the American Dental Association, vol. 86 (2), Feb. 1973; 409-411. https://doi.org/10.14219/jada.archive.1973.0081.

Bi et al; "Verification of accuracy of an algorithmic image-based dental pulp vitality test"; Medical Imaging 2020: Computer-Aided Diagnosis, edited by H. K. Hahn & M. A. Mazurowski (Eds.) , Proc. of SPIE vol. 11314, p. 145. https://doi.org/10.1117/12.2549744.

Gopikrishna, V. et al; (2009). "Assessment of pulp vitality: a review" International Journal of Paediatric Dentistry, 19 (1), 3-15. https://doi.org/10.1111/j.1365-263X.2008.00955.x.

Holland, G. R.; "Morphological features of dentine and pulp related to dentine sensitivity"; Archives of Oral Biology, vol. 39, Supplement, 1994, pp. S3-S11. https://doi.org/10.1016/0003-9969(94)90182-1.

Karayilmaz, H. et al.; "Comparison of the reliability of laser Doppler flowmetry, pulse oximetry and electric pulp tester in assessing the pulp vitality of human teeth"; (2011) Journal of Oral Rehabilitation, 38(5), 340-347. https://doi.org/10.1111/j.1365-2842.2010.02160.x.

Kwon, et al; "Thermal irritation of teeth during dental treatment procedures"; (2013), Restorative Dentistry & Endodontics, 38(3), 105. https://doi.org/10.5395/rde.2013.38.3.105.

Lejeune et al; "A review of odontogenic infections"; In The Journal of the Louisiana State Medical Society: official organ of the Louisiana State Medical Society; (1994), (vol. 146, Issue 6, pp. 239-241). https://pubmed.ncbi.nlm.nih.gov/8057047/ Abstract.

Matsutani et al; "Stimulation of the locus coeruleus suppresses trigeminal sensorimotor function in the rat"; Brain Research Bulletin, vol. 53 Issue 6, pp. 827-832, 2000. https://doi.org/10.1016/S0361-9230(00)00426-3.

Mendes et al; "Evaluation of magnetic resonance imaging for diagnostic purposes in operative dentistry-a systematic review"; Clinical Oral Investigations (vol. 24, Issue 2, pp. 547-557); 2020. Springer. https://doi.org/10.1007/s00784-019-03103-8.

Nagaoka et al; "Bacterial invasion into dentinal tubules of human vital and nonvital teeth"; Journal of Endodontics, 21 (2), 70-73. 1995. https://doi.org/10.1016/S0099-2399(06)81098-8.

Paphangkorakit et al; "Discrimination of hardness by human teeth apparently not involving periodontal receptors"; Archives of Oral Biology, vol. 43, Issue 1, Jan. 18, 1998, pp. 1-7. https://doi.org/10.1016/S0003-9969(97)00090-3.

Tymofiyeva et al; "High-resolution 3D magnetic resonance imaging and quantification of carious lesions and dental pulp in vivo"; Magnetic Resonance Materials in Physics, Biology and Medicine, 2009, 22(6), 365-374. https://doi.org/10.1007/s10334-009-0188-9.

Walsh, L.J.; "Serious complications of endodontic infections: Some cautionary tales" Australian Dental Journal, (1997) 42(3), 156-159. https://doi.org/10.1111/j. 1834-7819.1997.tb00113.x.

Yu, C et al; "An overview of the dental pulp: its functions and responses to injury"; Australian Dental Journal, 2007; 52 (1 Suppl), S4-S6. https://doi.org/10.1111/j.1834-7819.2007.tb00525.x.

"Pathways of the Pulp" 6 th Edition. Edited by: Cohen, Stephen and Burns, Richard C. Henry O. Trowbridge, & Kim, S. (n.d.). "Pulp development, structure and function." In: Cohen S, Burns RC, eds. Pathways of the Pulp. St. Louis: Mosby (1998th ed.). 1998. Retrieved Jul. 18, 2020, from https://www.academia.edu/16279447/Cohens_Pathways_of_the_Pulp_10th_ed._dentistry_-_K._Hargreaves_et._al.

* cited by examiner

DETECTING DISTANCE OF A PROBE TO PULP OF A TOOTH

This application is the U.S. National Phase application under 35 U.S.C. § 371 of International Application No. PCT/EP2021/085340, filed on Dec. 13, 2021, which claims the benefit of EP Application Serial No. 20214511.6, filed Dec. 16, 2020. These applications are hereby incorporated by reference herein.

FIELD OF THE INVENTION

The present invention relates to the field of oral treatment, and more particularly to concepts for detecting distance of a probe to pulp of a tooth.

BACKGROUND OF THE INVENTION

The dental pulp resides in a rigid chamber (i.e. a tooth) in the oral cavity comprising dentine, enamel and cementum. It fulfills the following essential functions: it increases the resistivity of the tooth to bacterial invasion; it acts as a warning mechanism due to its sensitivity to thermal and mechanical stimuli; and it provides a force feedback loop to masticatory muscles. However, the integrity of the dental pulp can be damaged by tooth decay or by the dental procedures required for the removal of tooth decay, such as drilling. Therefore, the ability to measure the distance to the pulp in the range from 2 mm to 0.2 mm is essential in order to prevent dental pulp damage during dental procedures, or to choose the correct treatment method for previously damaged dental pulp.

Whilst caries treatment is a simple and common process, 29% of deep caries treatments result in unintended dental pulp exposure. To fix the exposure of the dental pulp, root canal treatment must be undertaken, but such treatment is much more time-consuming and expensive than the initial caries treatment. Thus, there is a significant benefit associated with avoiding unintended pulp exposure.

The likelihood of unintended pulp exposure can be reduced from 29% to 18% by utilizing stepwise evacuation. However, stepwise evacuation can simultaneously result in additional discomfort to the patient, increased cost and increased risk of pulp exposure during the removal of temporary filling or final excavation. Moreover, treatment employing stepwise excavation requires multiple appointments, and thus increases risk of treatment failure (e.g. caused by patients not returning to the dentist to conclude their treatment). Stepwise excavation is thus not considered a suitable, long-term solution.

Current practices for measuring the distance to the pulp are predominantly subjective: the dentist applies his/her experience and knowledge of the tooth anatomy to the visual appearance of the tooth. Objective modes of measurement involve X-ray imaging, but this utilizes harmful ionizing radiation and provides limited views of the tooth.

US 2009/0155735 discloses dental apparatus including a white light interferometer, for determining distance to pulp of a tooth from its surface.

SUMMARY OF THE INVENTION

The invention is defined by the claims.

According to examples in accordance with an aspect of the invention, there is provided a method for detecting distance of a probe to pulp of a tooth by determining an indication of thickness of dentine of the tooth according to claim 1.

Proposed embodiments may enable the detection of the distance of a probe in contact with a tooth surface to pulp of the tooth by illuminating the dental tissue of the tooth. According to a proposed concept, data representing scattered light from the illuminated dental tissue can be received and used to obtain spectra of the scattered light. From analysis of the spectra, the distance to the pulp of the tooth from the tooth surface may be inferred. In this way, safe, objective and accurate measurement of the distance to dental pulp can be achieved. Proposed embodiments may, for example, be used during dental treatment to prevent unintended pulp exposure, particularly in treatments that involve drilling (such as caries treatment).

In particular, it has been realized that properties of the spectra of visible light reflected or scattered by the dentine of a tooth can be leveraged to detect the presence of blood (in the pulp of the tooth) behind a dentine thickness of up to 2 mm.

Investigations have shown that the absorption spectrum of the blood may be high in the wavelength range of 500 nm to 600 nm when the probe is close to the pulp. Further investigations have shown that the absorption spectrum of blood may display two absorption peaks: one around 540 nm and a second around 580 nm. The reflectivity spectra of visible light reflected or scattered by the dentine has also been investigated and displays troughs at 540 nm and 580 nm, which indicates that a reduced proportion of visible light is reflected from the dentine at these wavelengths. It is proposed that the visible light is absorbed by the blood of the pulp. Therefore, the absorption spectrum of the blood contained in the pulp of the tooth can be related to the reflectivity spectra of visible light reflected/scattered by the dentine of the tooth.

Investigations have also observed decreased reflectivity in the range 400 nm to 600 nm at a dentine thickness of 1 mm. It is suggested that dentine thicknesses within a comparable range (i.e. 0-2 mm) have similar reflectivity spectra.

At thinner dentine thicknesses (i.e. 0-2 mm), the visible light from the probe may pass through the dentine to the blood of the pulp. The blood absorbs substantially more light than the dentine, as is particularly evident in the wavelength range of 400 nm to 600 nm due to the presence of the blood absorption peaks. The visible light is absorbed by both the blood and the dentine and hence the absorption of visible light increases. Therefore, a lower proportion of light may be reflected back to the probe.

At thicker dentine thickness (i.e. greater than 2 mm), the visible light may not pass through the dentine to the blood of the pulp. Since dentine absorbs a reduced proportion of visible light when compared to the aforementioned combination of blood and dentine, an increased proportion of light is reflected from the dentine as a result. The threshold dentine thickness of 2 mm used in the previous scenarios is simply an example and may vary (within the range 1.5 mm to 2.5 mm for example).

To investigate further, the amplitude of the spectra in the range 400 nm to 600 nm was integrated and plotted alongside dentine thicknesses below about 2 mm. As the thickness of the dentine decreased, the integrated amplitude of the spectra also decreased, suggesting the variables may be proportional.

By leveraging these findings, it is proposed that the spectra and integrated amplitude of visible light reflected/scattered by a tooth can be used to determine a thickness of dentine (and thus provide an indication of distance from the dentine of the tooth to the pulp). Specifically, the thickness of dentine can be determined within three distinct ranges:

(i) If the integrated amplitude of the spectra in the range 400 nm to 600 nm exceeds a threshold value and the spectra does not display reflectivity troughs (i.e. light absorption peaks), then it can be determined no light is reaching the blood because it is all reflected by the dentine. It may then be inferred that the thickness of the dentine is in the range of about 2 mm to about 1 mm;

(ii) If the integrated amplitude of the spectra in the range 400 nm to 600 nm is lower than a threshold value and the spectra displays reflectivity troughs (i.e. light absorption peaks), then it can be determined that light is only partly reflected by the dentine and it reaches the blood. It may then be inferred that the thickness of the dentine is in the range about 1 mm to about 0.2 mm; and (iii) If the integrated amplitude of the spectra in the range 400 nm to 600 nm is lower than a threshold value and the spectra does not display reflectivity troughs (i.e. light absorption peaks), then it can be determined that all light is absorbed by the blood and no light is reflected by the dentine. The thickness of the dentine is thus thinner than about 0.2 mm, though this value may vary.

It should, however, be understood that there may be some variation in the distances detailed above. For example, the threshold of 2 mm detailed above may be within the range 1.75 mm to 2.25 mm. By way of further example, the amount of clinical variation in the thresholds detailed above (i.e. 0.2 mm, 1 mm and 2 mm) may be in the range of 10%-30%.

Conventional methods to determine the distance from the point of treatment to the dental pulp are mostly subjective and rely on the experience of the dentist. Specifically, the dentist must apply their knowledge of the tooth anatomy to the visual appearance of the tooth. However, the reliance on subjectivity may subsequently increases the risk of human error. Further, this risk is magnified if dentists lack sufficient experience. Using proposed embodiments, dentists may benefit from an objective measurement method that limits the risk of human error.

According to proposed embodiments, dentists may benefit from an objective measurement of a distance from a dental probe contacting a tooth surface to pulp of the surface that not only contains significantly more information than X-ray imaging, but also does not require harmful radiation for use. Further, by obtaining a single measurement indication or metric (e.g. an indication of the thickness of dentine between of a tooth-contacting probe to the pulp of a tooth), comparisons between subjects (e.g. patients) may be simpler to make.

Proposed embodiments may also greatly reduce the occurrence of unintended pulp exposure, thereby saving dentists both time and money.

By providing a robust method for determining an indication of the distance from a tooth surface to the tooth pulp, embodiments may replace the use of stepwise excavation.

Other embodiments may obtain a spectral analysis result from the spectra by determining slopes of the intensities of the spectra in the range of 300-800 nm, and hence may determine an indication of the thickness of the dentine of the tooth using the determined slopes of intensities. Using the determined slopes of intensities, a more reliable determination of thickness of tooth dentine between a probe (contacting the tooth surface) and the pulp of the tooth.

Further, embodiments may obtain the spectral analysis result from the spectra by detecting light absorption peaks within a wavelength range characteristic to a wavelength range of light absorption spectra of blood. Hence, an indication of the distance of the tooth-contacting probe to the pulp of the tooth may be determined using the detected light absorption peaks. Using the detected light absorption peaks, an indication of the thickness of tooth dentine between a probe (in contact with the tooth surface) and the pulp of the tooth may be more accurately determined.

Embodiments may use a wavelength range of light absorption spectra of blood within 520-550 nm and 570-590 nm. By restricting the wavelength range, the light absorption peak detection may be made more efficient.

A computer program product may comprise computer program code means which, when executed on a computing device having a processing system, cause the processing system to perform the previously explained method of detecting distance of a probe to pulp of a tooth.

In other embodiments, a method for preventing exposure of pulp of a subject's tooth during dental treatment may comprise illuminating dental tissue of the subject's tooth with broadband visible light and detecting visible light reflected from the dental tissue. The method for preventing exposure of pulp of a subject's tooth may also comprise analyzing the spectra of the detected visible light reflected from the dental tissue to obtain a spectral analysis result, and also generating an indication of a distance to the pulp of the subject's tooth (e.g. indication of thickness of dentine between tooth-contacting probe and the tooth pulp) based on the spectral analysis result.

Further, embodiments may comprise a method for analyzing the spectra of the detected visible light reflected from the dental tissue. The method may comprise determining an intensity of the spectra of the detected visible light in the range of 400-800 nm.

Additionally, the method may analyze the variation of amplitude of the detected visible light with respect to wavelength to detect light absorption peaks in the range of 400-800 nm. The method may also comprise determining the spectral analysis result based on the determined intensity of the spectra and the detection results.

Embodiments may utilize a method that analyses the variation of amplitude of the detected visible light with respect to wavelength to detect light absorption peaks in the range of 300-800 nm using the following process. Light absorption peaks in the range of 300-800 nm may be detected by observing first and second troughs in the variation of amplitude of the detected visible light in the ranges of 520-550 nm and 570-590 nm, respectively. Preferably, first and second troughs in the variation of amplitude of the detected visible light may be observed at 540 nm and 580 nm, respectively.

Other embodiments may comprise a method wherein determining an intensity of the spectra of the detected visible light in the range of 300-800 nm comprises performing an integration operation.

Further, the method of determining the spectral analysis may comprise the following process. A distance to the pulp of the subject's tooth in the range of 1-2 mm may be determined as the spectral analysis result, responsive to the determined intensity exceeding a threshold value and the detection of no light absorption peaks. Additionally, a distance to the pulp of the subject's tooth in the range of 0.2-1 mm may be determined as the spectral analysis result, responsive to the determined intensity not exceeding the threshold value and the detection of light absorption peaks.

Finally, a distance to the pulp of the subject's tooth less than 0.2 mm may be determined as the spectral analysis result, responsive to the determined intensity not exceeding the threshold value and the detection of no light absorption peaks.

A computer program product may comprise computer program code means which, when executed on a computing device having a processing system, cause the processing system to perform the previously explained method for determining distance of a probe to pulp of a tooth by determining a thickness of dentine of the tooth.

Additionally, embodiments may comprise dental apparatus for determining distance of a probe to pulp of a tooth by determining a thickness of dentine of the tooth according to claim 6.

Further, embodiments may obtain a spectral analysis result from the spectra by determining intensities of the spectra in the range of 300-800 nm. By only determining intensities across a specified range, the processor may perform its function more quickly.

Embodiments may obtain a spectral analysis result from the spectra by detecting light absorption peaks with a wavelength range characteristic to a wavelength range of absorption spectra of blood. By adhering to the aforementioned process, the blood absorption peaks may be identified, enabling the more precise detection of distance to the pulp.

Other embodiments may use wavelength ranges of absorption spectra of blood of 520-550 nm and 570-590 nm. Hence the absorption peaks may be identified more quickly.

Proposed embodiments may prevent the exposure of pulp of a subject's tooth during dental treatment using apparatus, wherein the apparatus comprise a dental probe, a spectral analysis component and a processor. The dental probe may be configured, in use, to illuminate the dental tissue and detect the visible light reflected from the dental tissue. The spectral analysis component may then analyze the spectra of the reflected light to produce a result that the processor may use to generate an indication of a distance from the probe, when in contact with the tooth, to the pulp of the subject's tooth. The indication may be visible, audible, vibrational, and other ways that includes human senses.

Other embodiments may employ a concept wherein the spectral analysis component is configured to adhere to the following process. Initially, an intensity of the spectra of the detected visible light in the range of 300-800 nm may be determined. The variation of amplitude of the detected visible light with respect to wavelength may then be analyzed to detect light absorption peaks in the range of 300-800 nm. Finally, the spectral analysis result may be determined based on the intensity of the spectra and the detection results. By adhering to the aforementioned process, the light absorption peaks may be identified, enabling the more precise detection of distance to the pulp.

Embodiments may configure the spectral analysis component to detect light absorption peaks in the range of 300-800 nm by observing first and second troughs in the variation of amplitude of the detected visible light in the ranges of 520-550 nm and 570-590 nm, respectively. Preferably, first and second troughs in the variation of amplitude of the detected visible light may be observed at 540 nm and 580 nm, respectively. Analyzing the variation of amplitude of detected visible light in a further limited range may enable the quicker identification of troughs, and hence enable an accelerated determination of the indication of the distance to the pulp (i.e. thickness of dentine between tooth-contacting probe and the pulp).

Embodiments may also configure the spectral analysis component to determine an intensity of the spectra of the detected visible light in the range of 300-800 nm by performing an integration operation. Calculating the integrated amplitude of the intensity spectra may enable the determination of distance from the dental pulp to be more precise.

Additionally, embodiments may employ a concept wherein the spectral analysis component is configured to determine, as the spectral analysis result, a distance to the pulp of the subject's tooth in the range of 1-2 mm, responsive to the determined intensity exceeding a threshold value and the detection of no light absorption peaks. The spectral analysis component may also be configured to determine, as the spectral analysis result, a distance to the pulp of the subject's tooth in the range of 0.2-1 mm, responsive to the determined intensity not exceeding the threshold value and the detection of light absorption peaks. Further, the spectral analysis may be configured to determine, as the spectral analysis result, a distance to the pulp of the subject's tooth less than 0.2 mm, responsive to the determined intensity not exceeding the threshold value and the detection of no light absorption peaks. By having clearly defined measurement regions, the spectral analysis component may convey significant distances from the pulp e.g. 2 mm, 1 mm, 0.2 mm to the probe. Consequently, as the probe measures in real time, it may indicate warning mechanisms to the dentist, such that the dentist is aware of a rough distance the probe is from the dental pulp.

In some embodiments, the dental probe may comprise an optical waveguide configured to receive broadband visible light and to guide the received broadband visible light to a first light emission portion of the optical waveguide. The waveguide may then be adapted, in use, to be positioned in close proximity to the dental tissue of the subject's tooth. The implementation of an optical waveguide may enable precise control over the exposure of visible light to the dental tissue, ensuring that the dentine is illuminated.

Other embodiments may further configure the optical waveguide to receive visible light reflected from the dental tissue and to guide the received visible light reflected from the dental tissue to the spectral analysis component. Hence, only a single optical waveguide may be required for both the emission of visible light to the dental tissue and detection of the light reflected from the subject's dental tissue.

Embodiments may employ a concept, wherein the optical waveguide comprises an optical fibre and a beamsplitter. A beamsplitter may enable the implementation of a dental probe with a single optical fibre, since the beamsplitter allows both the emitted and reflected visible light ray to occupy the same optical fibre.

According to another aspect of the invention, there is provided a drill comprising a dental apparatus according to a proposed embodiment.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
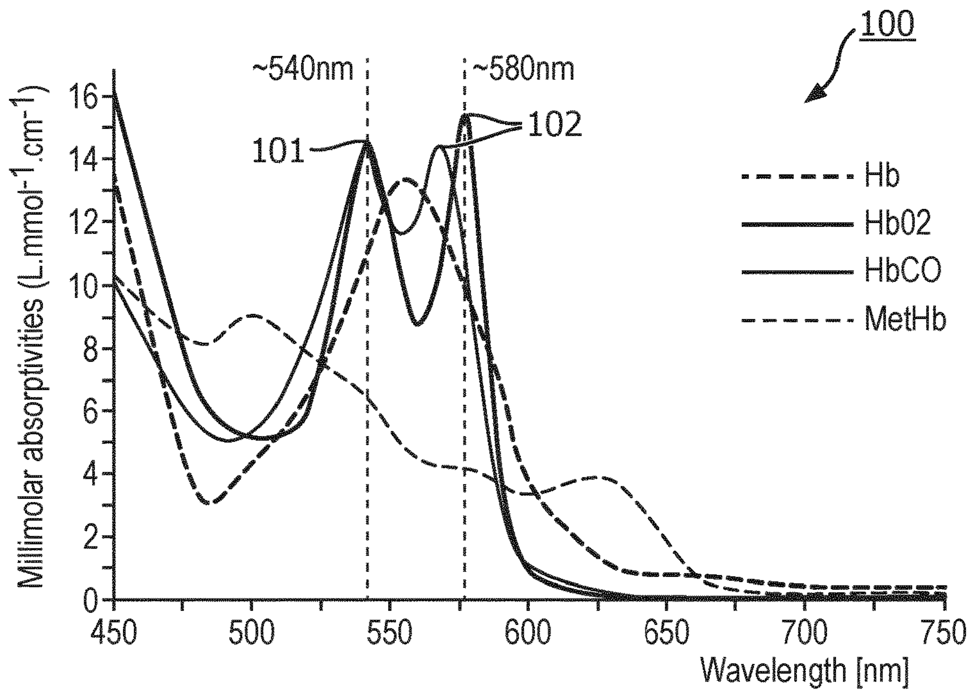
FIG. 1 shows absorption spectra of blood.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. The mere fact that certain measures are recited in mutually different dependent claims does not indicate that a combination of these measures cannot be used to advantage. It should be understood that the Figures are merely schematic and are not drawn to scale. It should also be understood that the same reference numerals are used throughout the Figures to indicate the same or similar parts.

Implementations in accordance with the present disclosure relate to various systems, adaptations and/or methods of detecting an indication of the distance of a tooth-contacting probe to pulp of a tooth, pertaining to preventing pulp exposure during dental treatment. According to proposed concepts, a number of possible solutions may be implemented separately or jointly. That is, although these possible solutions may be described below separately, two or more of these possible solutions may be implemented in one combination or another.

Proposed embodiments may provide a method for detecting an indication of the distance of a probe (in contact with a tooth) to pulp of the tooth. Embodiments may therefore be used for the prevention of unintended pulp exposure. Embodiments utilize a dental probe to contact a tooth surface and illuminate the dental tissue of the tooth. Data representing scattered light from the dental tissue is then received and a spectra of the scattered light is obtained. A spectral analysis result is then obtained from the spectra, and a distance of the probe to the pulp of the tooth is inferred based on the spectral analysis result.

In particular, it has been realized that properties of the spectra of visible light reflected or scattered by the dentine of a tooth can be leveraged to detect the presence of blood (that would be contained in the pulp of the tooth) behind a dentine thickness of up to 2 mm.

Investigations have shown that the absorption spectra of the blood may be high in the wavelength range of 500 nm to 600 nm, as demonstrated in FIG. 1.

FIG. 1 shows absorption spectra of blood 100, wherein the horizontal axis displays wavelength (nm) and the vertical axis displays millimolar absorptivities ($L \cdot mmol^{-1} \cdot cm^{-1}$). Further investigations have shown that the absorption spectra of blood may display two absorption peaks: one at roughly 540 nm and a second at roughly 580 nm, such that the peaks often fall within the range 520-550 nm and 570-590 nm. As observed in FIG. 1, the peak 101 occurs at a wavelength of −540 nm and the peaks 102 occur either side of a wavelength of −580 nm. Hence FIG. 1 is in agreement with the aforementioned investigations.

Figure 2:
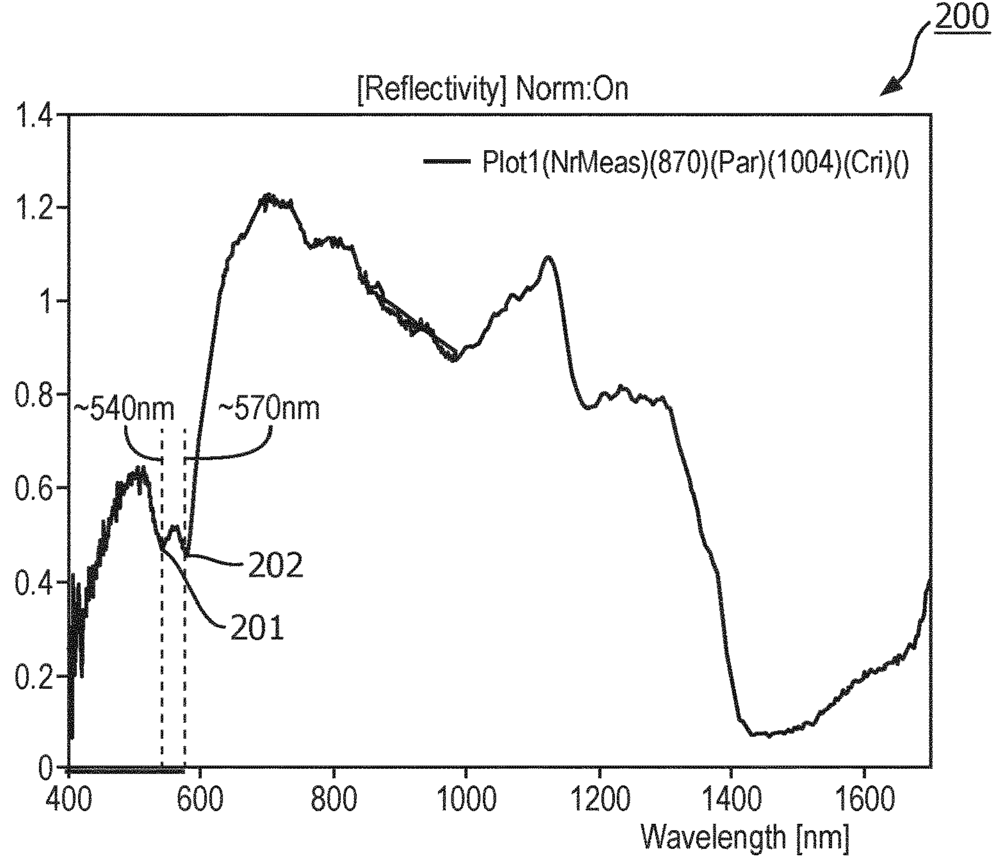
FIG. 2 shows a measured reflectivity spectrum for the case of a 1 mm thick slice of dentine.

The reflectivity spectra of visible light reflected or scattered by the dentine have also been investigated and a reflectivity spectrum is shown in FIG. 2.

FIG. 2 shows a reflectivity spectrum 200 for the case of a 1 mm thick slice of dentine, wherein the horizontal axis displays wavelength (nm) and the vertical axis displays reflectivity (arbitrary units). Troughs in reflectivity can be observed in FIG. 2: the trough 201 occurs at −540 nm and a second trough 202 occurs at −580 nm. A trough in reflectivity suggests a reduced proportion of visible light is reflected from the dentine at these wavelengths. Further, the absorption peaks 101, 102 occur at very similar wavelengths to the reflectivity troughs 201, 202, and reflectivity is also decreased in the range 400 nm to 600 nm, which coincides with increased absorption shown in FIG. 1 in the range 450 nm to 600 nm. It may be thus inferred that the visible light is absorbed by the blood of the pulp. Therefore, the absorption spectrum of the blood contained in the pulp of the tooth can be related to the reflectivity spectra of visible light reflected/scattered by the dentine of the tooth, such that absorption peaks correspond to reflectivity troughs.

Investigations have also shown that dentine thicknesses thinner than 2 mm can exhibit decreased absorption and hence increased reflectivity in the range 400 nm to 600 nm, and that the variables may be dependent.

Figures 3, 4:
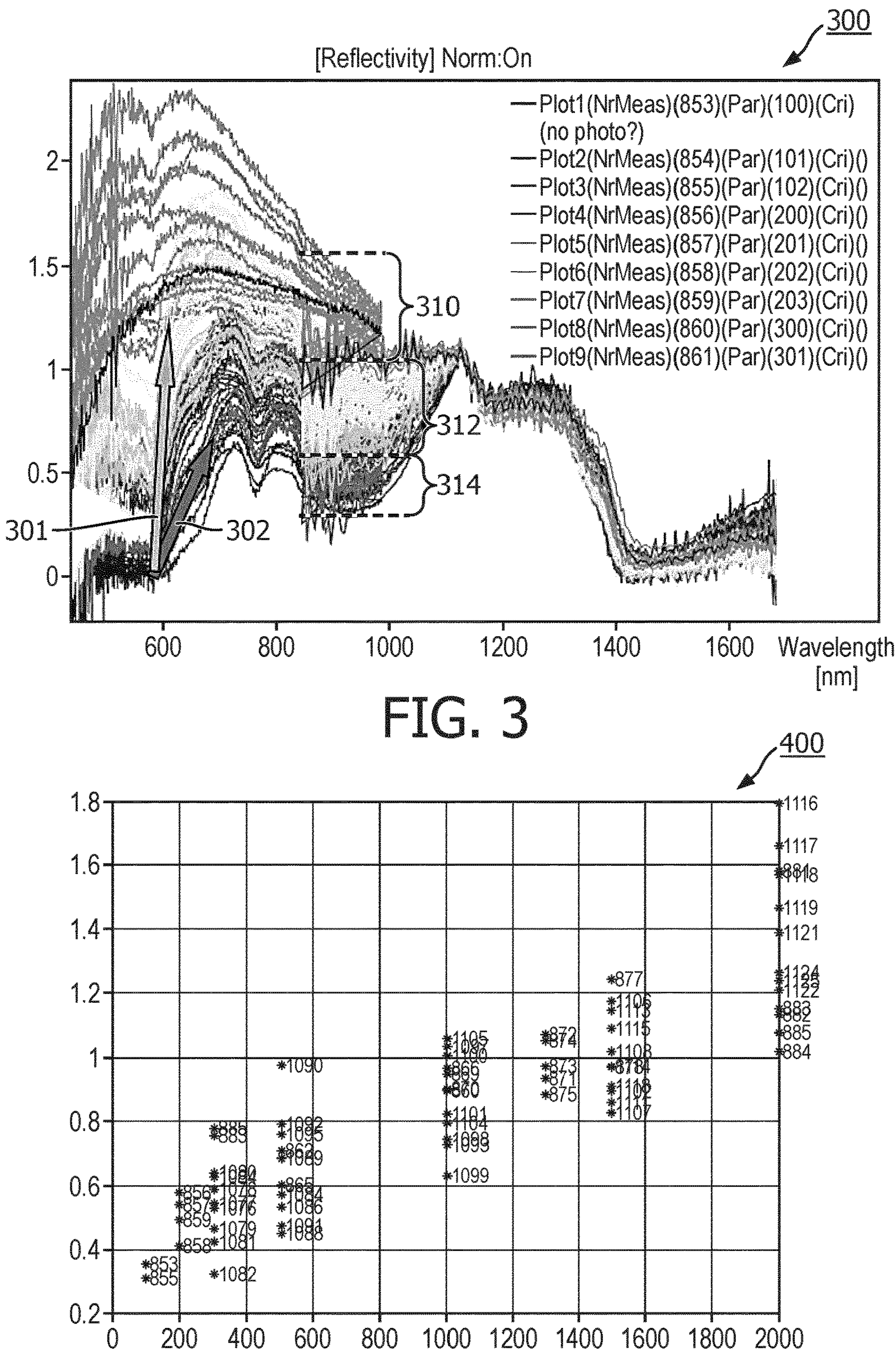
FIG. 3 shows measured reflectivity spectra for a range of dentine thicknesses.
FIG. 4 shows an integrated amplitude plot for a range of dentine thicknesses.

FIG. 3 shows measured reflectivity spectra 300 for a range of dentine thicknesses, wherein the horizontal axis displays wavelength (nm) and the vertical axis displays reflectivity (arbitrary units). Further, the shading of the line 310, 312, 314 indicates different dentine thicknesses, wherein 310 indicates a high dentine thickness, 312 indicates a medium dentine thickness and 314 indicate indicates a low dentine thickness. From FIG. 3, it is evident that lower dentine thicknesses have lower reflectivities. Additionally, the slopes 301, 302 of the spectra can help to determine the distance to the pulp (i.e. dentine thickness).

To investigate further, the amplitude of the spectra from FIG. 3 (in the range 400 nm to 600 nm) was integrated and plotted as a function of the dentine thicknesses below 2 mm, shown in FIG. 4.

FIG. 4 shows an integrated amplitude plot 400 for a range of dentine thicknesses, wherein the horizontal axis displays the distance to the pulp (microns) and the vertical axis displays the integrated amplitude (arbitrary units). As the thickness of the dentine decreases, the integrated amplitude of the spectra also decreases, suggesting the variables may be proportional.

By leveraging these findings, it is proposed that the spectra and integrated amplitude of visible light reflected/scattered by a tooth can be used to determine an indication of thickness of dentine (and thus provide an indication of distance from the tooth surface to the pulp). Specifically, the thickness of dentine can be determined to within three distinct ranges:

(i) If the integrated amplitude of the spectra in the range 400 nm to 600 nm exceeds a threshold value and the spectra does not display reflectivity troughs (i.e. light absorption peaks), then it can be determined no light is reaching the blood because it is all reflected by the dentine. The thickness of the dentine is thus in the range 2 mm to 1 mm.

(ii) If the integrated amplitude of the spectra in the range 400 nm to 600 nm is lower than a threshold value and the spectra displays reflectivity troughs (i.e. light absorption peaks), then it can be determined that light is only partly reflected by the dentine and it reaches the blood. The thickness of the dentine is thus in the range 1 mm to 0.2 mm.

(iii) If the integrated amplitude of the spectra in the range 400 nm to 600 nm is lower than a threshold value and the spectra does not display reflectivity troughs (i.e. light absorption peaks), then it can be determined that all light is absorbed by the blood and no light is reflected by the dentine. The thickness of the dentine is thus thinner than 0.2 mm.

Figure 5:
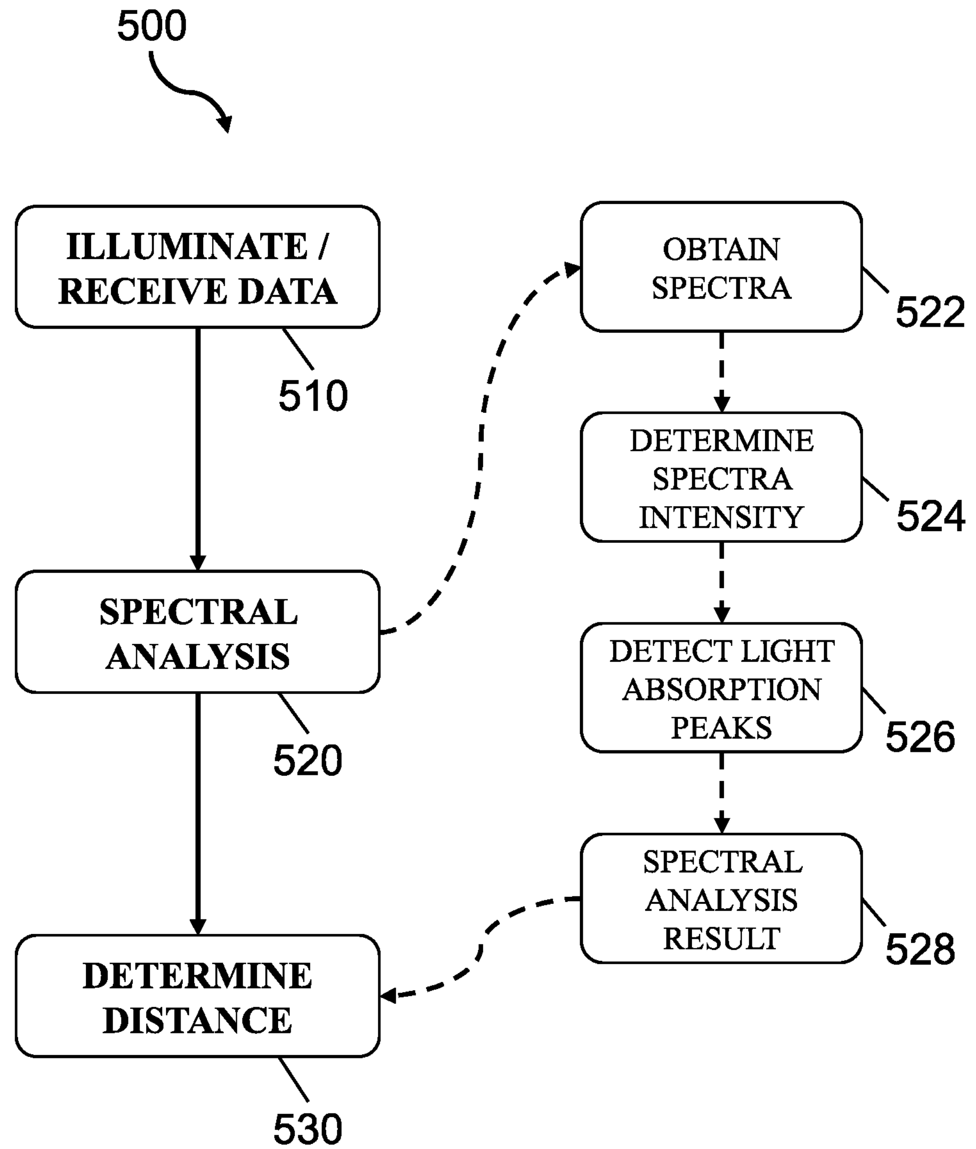
FIG. 5 shows a method for preventing exposure of pulp of a subject's tooth during dental treatment.

FIG. 5 shows a method for detecting distance of a probe to pulp of a tooth 500 according to proposed embodiments. The method comprises steps 510, 520 and 530. In step 510, the dental tissue of the tooth is illuminated by a probe placed in contact with the tooth surface, and the data representing scattered light from the dental tissue is received. In step 520, a spectra of the scattered light is obtained 522 and then analyzed 524, 526 to obtain a spectral analysis result 528. In step 530, the distance of the probe to the pulp of the tooth is determined, based on the spectral analysis result 528.

Spectral analysis 520 comprises the method laid out by the steps 522, 524, 526 and 528. In step 522, the spectra is obtained in the wavelength range of 300-800 nm. It should be noted that the scattered light comprises light having a wavelength range of 300-800 nm. In step 524, the intensity of the spectra is determined in the range of 300-800 nm. In step 526, light absorption peaks are detected, wherein the light absorption peaks have a wavelength range characteristic to a wavelength range of light absorption spectra of blood. The wavelength range of light absorption spectra of blood is within 520-540 nm and 550-570 nm. In step 528, the spectral analysis result is obtained by determining intensities of the spectra 524 and by detecting light absorption peaks with wavelength range characteristic to a wavelength range of light absorption spectra of blood 526. In step 530, an indication of the distance of the probe to the pulp of the tooth is determined using the determined intensities in step 524 and the detected light absorption peaks in step 526.

Figure 6:
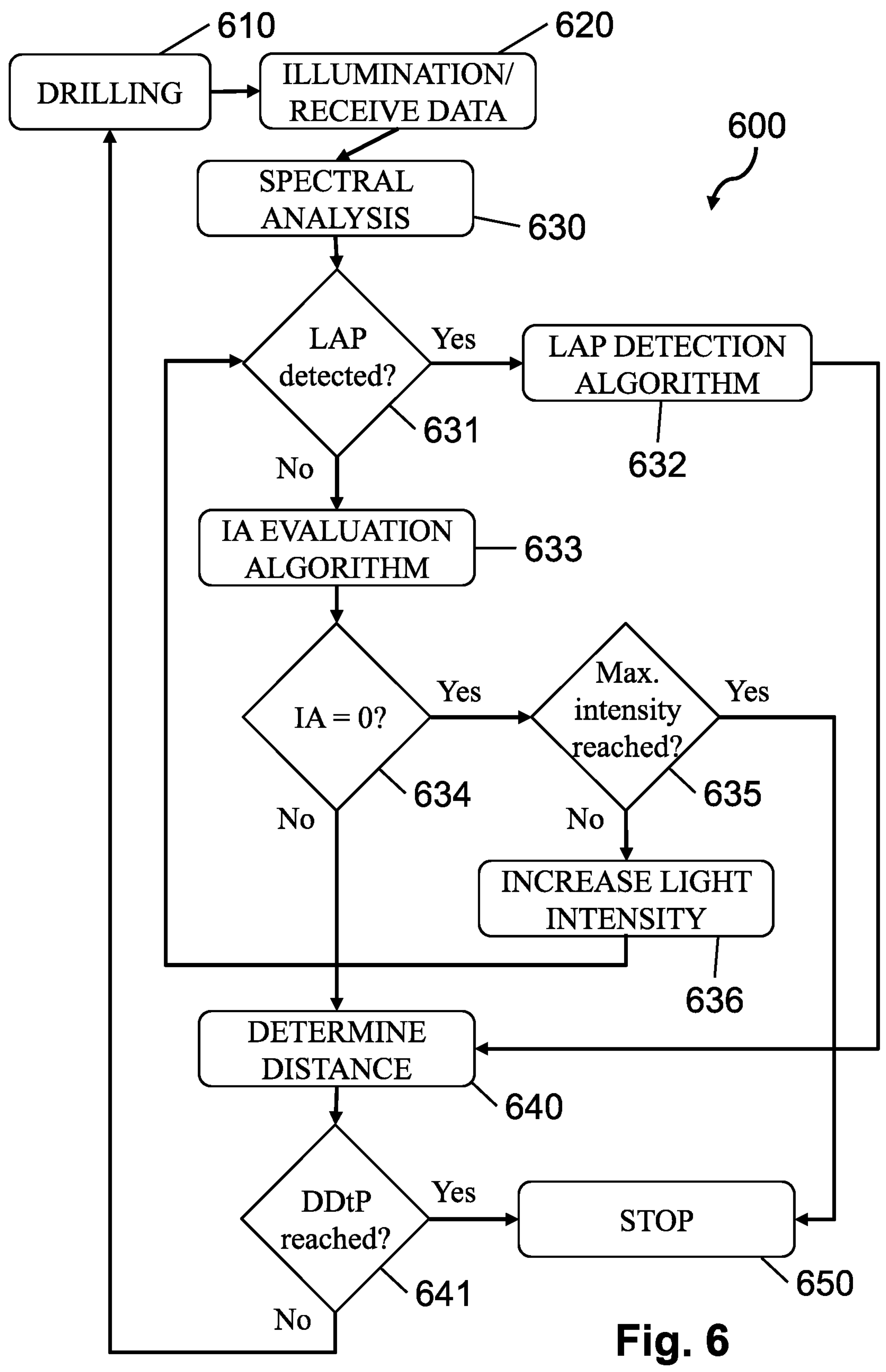
FIG. 6 shows a proposed method for preventing exposure of pulp of a subject's tooth during dental drilling.

FIG. 6 shows a proposed method for detecting distance of a probe (in contact with a tooth) to pulp of the tooth 600 during dental drilling, according to proposed embodiments. The proposed method makes use of optical spectroscopy, wherein a light source is used to illuminate tissue through fiber optics. The light is scattered and absorbed in the tissue, and the reflected light is then collected and guided by another or the same fiber to a spectrometer.

The method 600 comprises the steps 610, 620, 630, 640 and 650. In step 610, the dental drilling commences on the dental tissue of the tooth. In step 620, the dental tissue of the tooth is illuminated with light by the probe and data representing scattered light from the dental tissue is received. It should be noted the scattered light comprises light having a wavelength range of 300-800 nm. In step 630, the spectra of the scattered light from the dental tissue is obtained and then analyzed to obtain a spectral analysis result. In step 640, the distance of the probe to the pulp of the tooth is determined based on the spectral analysis result. In step 650, if the desired distance to the pulp is reached, then drilling is stopped.

The method of spectral analysis 630 further comprises steps 631, 632, 633, 634, 635 and 636. To start, step 630 involves initially obtaining a spectra in the wavelength range of 300-800 nm, and then determining intensities of the spectra in the range of 300-800 nm. The spectra comprises a measured reflectivity spectra generated by a spectrometer.

In step 631, light absorption peaks are detected, wherein the light absorption peaks have a wavelength range characteristic to a wavelength range of light absorption spectra of blood. The method of light absorption peak detection comprises analyzing the previously generated measured reflectivity spectra and observing troughs in the variation of amplitude within wavelength ranges. The troughs act as an indication that light is absorbed by the blood and hence correspond to light absorption peaks. If light absorption peaks are detected, then the light absorption peak algorithm 632 is applied. If light absorption peaks are not detected, then the integrated amplitude evaluation algorithm 633 is applied.

In step 632, the Light Absorption Peak (LAP) algorithm is applied. To start, light absorption peaks in the range of 300-800 nm are detected. The wavelength range of light absorption spectra of blood is applied; hence light absorption peaks should be observed within 520-550 nm and 570-590 nm. The light absorption peaks correspond to first and second troughs in the variation of amplitude of the spectra within 520-550 nm and 570-590 nm, respectively. Preferably, first and second troughs in the variation of amplitude of the spectra are observed at 550 nm and 580 nm, respectively. The light absorption peak algorithm uses the fact that the absorption of light by blood has two well-defined peaks around 540 nm and 580 nm, since when the probe is close to the pulp, more blood will absorb light, hence the amplitude of the spectra will show a sharp decrease around these wavelengths. The relative decrease in amplitude is a measurement of distance to the pulp. By fitting the spectra, the relative decrease and hence distance to the pulp can be estimated. The light absorption peak detection algorithm 632 enables the determination of distance of the probe to the pulp of the tooth 640.

In step 633, an integration operation is performed on the determined intensity of the spectra of the scattered light in the range of 300-800 nm. If the probe is close to the pulp, absorption will take place and hence the integrated value of intensity will decrease.

In step 634, the integrated amplitude value is analyzed. If the integrated amplitude value is not equal to zero, then the integrated amplitude value can be compared with a threshold value to determine the distance from the dental probe to the pulp 640. If the integrated amplitude value is equal to zero, then the light intensity of the probe must be increased, yet this depends on whether the maximum light intensity has already been reached 635.

In step 635, it is determined whether the maximum light intensity of the probe has been reached. If the maximum light intensity has not yet been reached, then there is insufficient light intensity to produce an integrated amplitude above zero. Hence the light intensity of the probe must be increased 636. If the maximum light intensity of the probe has been reached, then the integrated amplitude value is zero because the light is absorbed by the blood. Therefore, the drill is at the closest safe drilling distance and should not drill any further, hence drilling must stop 650 in order to avoid pulp exposure.

In step 636, the light intensity of the probe is increased and the light absorption peak detection of step 631 is repeated.

In step 640, the distance of the probe to the pulp of the tooth is determined using the determined intensities and detected light absorption peaks. The following criteria are given to determine the distance of the probe to the pulp of the tooth. If the integrated amplitude value is above a certain threshold value and blood peaks are not detected, then no light is reaching the blood because it is all reflected by the dentine, hence the distance to the pulp is in the range 2-1 mm. If the integrated amplitude is lower than a certain threshold value and blood peaks are detected, then light is only partly reflected by the dentine and it reaches the blood, hence the distance to the pulp is in the range 1-0.2 mm. If the integrated amplitude is lower than a certain threshold value and blood peaks are not detected, then all light is absorbed by the blood and no light comes back to the probe, hence the distance to the pulp is below 0.2 mm. This is the closest safe drilling distance to avoid pulp exposure. A more precise distance to the pulp may be determined by looking up the value of either the integrated amplitude or the blood peak detection parameter in a look-up table that correlates the measured parameter with a known dentine slice thickness.

In step 641, the desired distance to the pulp is compared with the distance of the probe to the pulp of the tooth previously determined in step 640. If the determined distance has reached the desired distance to the pulp, then drilling stops 650. If the determined distance has not yet reached the desired distance to the pulp, then drilling 610 continues and the method 600 is repeated.

Figure 7:
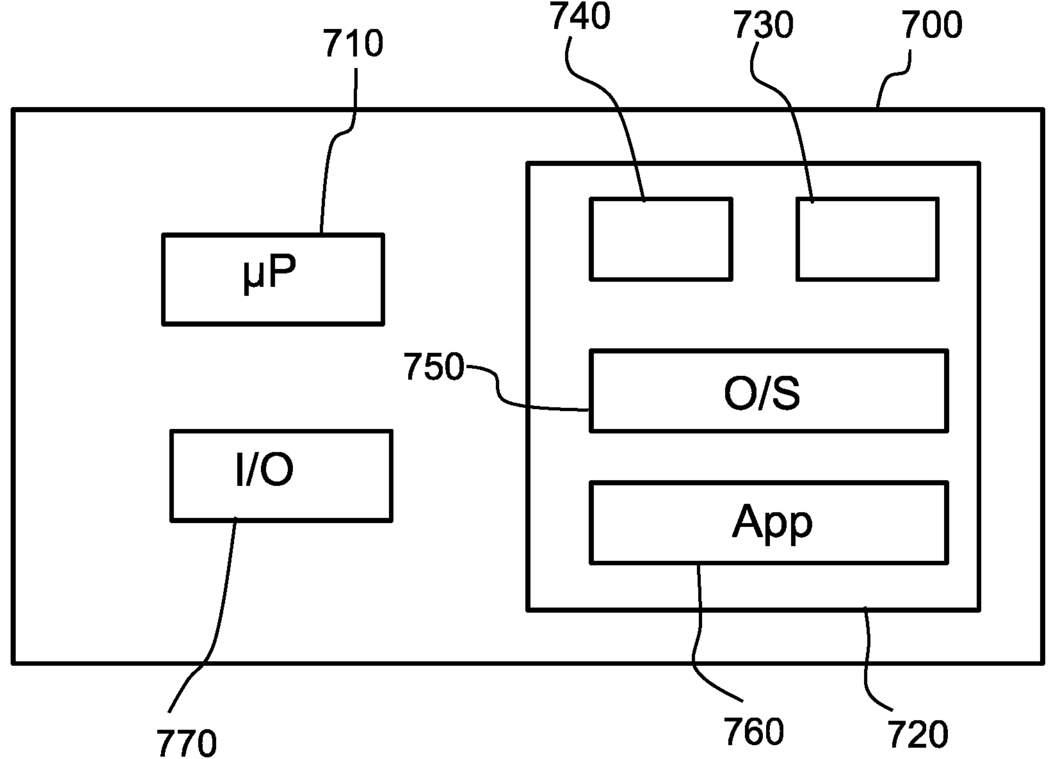
FIG. 7 illustrates an example of a computer within which one or more parts of an embodiment may be employed.

By way of further example, FIG. 7 illustrates an example of a computer 700 within which one or more parts of an embodiment may be employed. Various operations discussed above may utilize the capabilities of the computer 700. For example, for indicating a capability of respiratory muscles of a subject may be incorporated in any element, module, application, and/or component discussed herein. In this regard, it is to be understood that system functional blocks can run on a single computer or may be distributed over several computers and locations (e.g. connected via internet).

The computer 700 includes, but is not limited to, PCs, workstations, laptops, PDAs, palm devices, servers, storages, and the like. Generally, in terms of hardware architecture, the computer 700 may include one or more processors 710, memory 720, and one or more I/O devices 770 that are communicatively coupled via a local interface (not shown). The local interface can be, for example but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the aforementioned components.

The processor 710 is a hardware device for executing software that can be stored in the memory 720. The processor 710 can be virtually any custom made or commercially available processor, a central processing unit (CPU), a digital signal processor (DSP), or an auxiliary processor among several processors associated with the computer 700, and the processor 710 may be a semiconductor based microprocessor (in the form of a microchip) or a microprocessor.

The memory 720 can include any one or combination of volatile memory elements (e.g., random access memory (RAM), such as dynamic random access memory (DRAM), static random access memory (SRAM), etc.) and nonvolatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 720 may incorporate electronic, magnetic, optical, and/or other types of storage media. Note that the memory 720 can have a distributed architecture, where various components are situated remote from one another, but can be accessed by the processor 710.

The software in the memory 720 may include one or more separate programs, each of which comprises an ordered listing of executable instructions for implementing logical functions. The software in the memory 720 includes a suitable operating system (O/S) 750, compiler 740, source code 730, and one or more applications 760 in accordance with exemplary embodiments. As illustrated, the application 760 comprises numerous functional components for implementing the features and operations of the exemplary embodiments. The application 760 of the computer 700 may represent various applications, computational units, logic, functional units, processes, operations, virtual entities, and/or modules in accordance with exemplary embodiments, but the application 760 is not meant to be a limitation.

The operating system 750 controls the execution of other computer programs, and provides scheduling, input-output control, file and data management, memory management, and communication control and related services. It is contemplated by the inventors that the application 760 for implementing exemplary embodiments may be applicable on all commercially available operating systems.

Application 760 may be a source program, executable program (object code), script, or any other entity comprising a set of instructions to be performed. When a source program, then the program is usually translated via a compiler (such as the compiler 740), assembler, interpreter, or the like, which may or may not be included within the memory 720, so as to operate properly in connection with the O/S 750. Furthermore, the application 760 can be written as an object oriented programming language, which has classes of data and methods, or a procedure programming language, which has routines, subroutines, and/or functions, for example but not limited to, C, C++, C #, Pascal, BASIC, API calls, HTML, XHTML, XML, ASP scripts, JavaScript, FORTRAN, COBOL, Perl, Java, ADA, .NET, and the like.

The I/O devices 770 may include input devices such as, for example but not limited to, a mouse, keyboard, scanner, microphone, camera, etc. Furthermore, the I/O devices 770 may also include output devices, for example but not limited to a printer, display, etc. Finally, the I/O devices 770 may further include devices that communicate both inputs and outputs, for instance but not limited to, a NIC or modulator/demodulator (for accessing remote devices, other files, devices, systems, or a network), a radio frequency (RF) or other transceiver, a telephonic interface, a bridge, a router, etc. The I/O devices 770 also include components for communicating over various networks, such as the Internet or intranet.

If the computer 700 is a PC, workstation, intelligent device or the like, the software in the memory 720 may further include a basic input output system (BIOS) (omitted for simplicity). The BIOS is a set of essential software routines that initialize and test hardware at startup, start the O/S 750 and support the transfer of data among the hardware devices. The BIOS is stored in some type of read-only-memory, such as ROM, PROM, EPROM, EEPROM or the like, so that the BIOS can be executed when the computer 700 is activated.

When the computer 700 is in operation, the processor 710 is configured to execute software stored within the memory 720, to communicate data to and from the memory 320, and to generally control operations of the computer 700 pursuant to the software. The application 760 and the 750 are read, in whole or in part, by the processor 710, perhaps buffered within the processor 710, and then executed.

When the application 760 is implemented in software it should be noted that the application 360 can be stored on virtually any computer readable medium for use by or in connection with any computer related system or method. In the context of this document, a computer readable medium may be an electronic, magnetic, optical, or other physical device or means that can contain or store a computer program for use by or in connection with a computer related system or method.

The application 760 can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. In the context of this document, a "computer-readable medium" can be any means that can store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

A single processor or other unit may fulfill the functions of several items recited in the claims.

It will be understood that the disclosed methods are computer-implemented methods. As such, there is also proposed a concept of a computer program comprising code means for implementing any described method when said program is run on a processing system.

The skilled person would be readily capable of developing a processor for carrying out any herein described method. Thus, each step of a flow chart may represent a different action performed by a processor, and may be performed by a respective module of the processing processor.

As discussed above, the system makes use of a processor to perform the data processing. The processor can be implemented in numerous ways, with software and/or hardware, to perform the various functions required. The processor typically employs one or more microprocessors that may be programmed using software (e.g. microcode) to perform the required functions. The processor may be implemented as a combination of dedicated hardware to perform some functions and one or more programmed microprocessors and associated circuitry to perform other functions.

Examples of circuitry that may be employed in various embodiments of the present disclosure include, but are not limited to, conventional microprocessors, application specific integrated circuits (ASICs), and field-programmable gate arrays (FPGAs).

In various implementations, the processor may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor.

Figure 8:
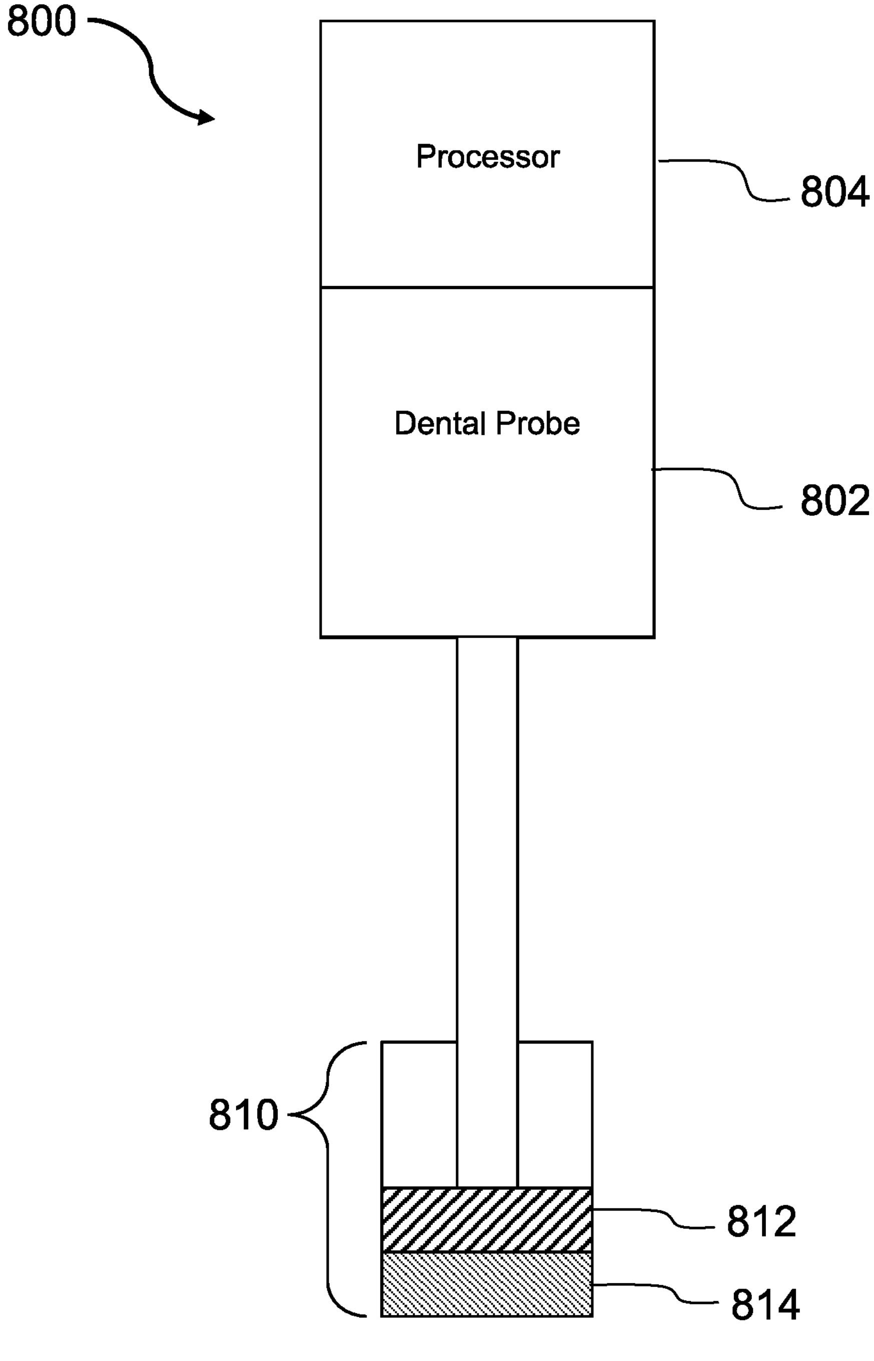
FIG. 8 shows a dental apparatus for determining distance of a probe to pulp of a tooth.

FIG. 8 shows a dental apparatus 800 for determining distance of a probe 802 to pulp 814 of a tooth 810 according to a proposed embodiment. The apparatus comprises a probe 802 and a processor 804. The probe 802 is configured to illuminate dental tissue of the tooth 810 with light and to detect scattered light from the dental tissue. The tooth 810 comprises dentine 812 and pulp 814. The dental tissue of the tooth is illuminated with light, wherein the light comprises at least two different colors and has a wavelength range of 300-800 nm.

The processor 804 is configured to obtain the spectra of the detected scattered light; to obtain a spectral analysis result from the spectra and to determine a distance of the probe 802 to the pulp 814 of the tooth 810 based on the spectral analysis result. It should be noted that spectra equate to intensities of at least two optical wavelengths. The processor 804 is configured to obtain the spectra of the detected scattered light in the wavelength range of 300-800 nm. To obtain a spectral analysis result from the spectra, the intensity of the spectra is determined in the range of 300-800 nm, wherein determining intensity also comprises determining intensity as part of the spectra. Further, to obtain a spectral analysis result from the spectra, light absorption peaks are detected, wherein the light absorption peaks have a wavelength range characteristic to a wavelength range of absorption spectra of blood. The wavelength ranges of absorption spectra of blood are within 520-540 nm and 550-570 nm.

Figure 9:
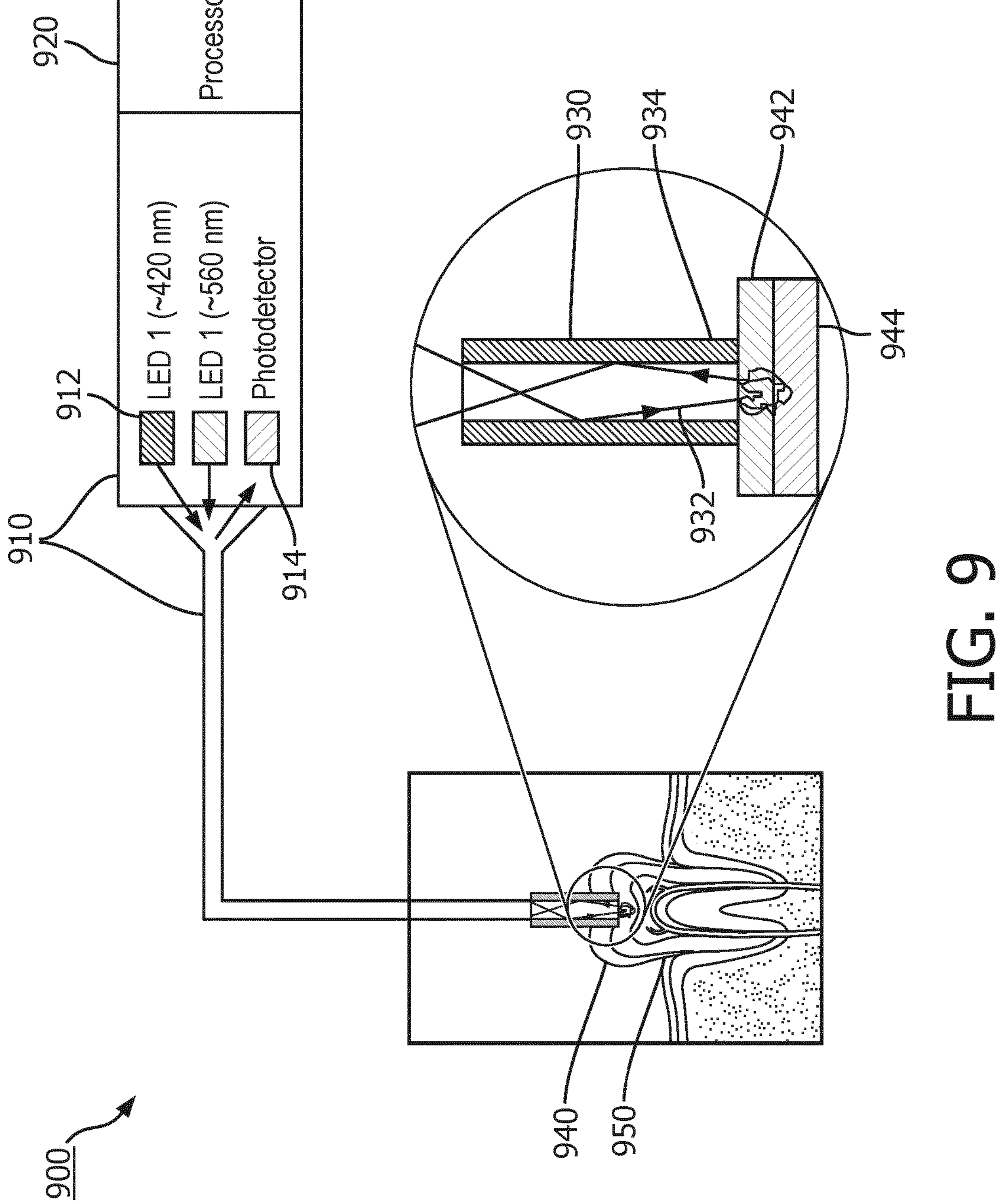
FIG. 9 shows a proposed dental apparatus for determining distance of a probe to pulp of a tooth.

FIG. 9 shows a proposed dental apparatus 900 for determining distance of a probe 910 to pulp 944 of a tooth 940. The apparatus comprises a dental probe 910 and a processor 920. The dental probe 910 comprises an optical fibre 930 and is positioned, in use, in close proximity to the dental tissue of a tooth 940, which is affixed to a gumline 950. The dental tissue of the tooth comprises dentine 942 and pulp 944.

The dental probe 910 is configured to illuminate dental tissue of the tooth 940 with light and to detect scattered light from the dental tissue, wherein the light must comprise at least two different colors. Hence, the dental probe 910 comprises a light source 912 to emit light rays and a spectrometer 914 to detect scattered light rays from the dental tissue. The light comprises having a wavelength range of 300-800 nm. In a proposed embodiment, the light source 912 comprises a light emitting diode (LED) and the spectrometer 914 comprises a photodetector. Additionally the dental probe 910 comprises an optical fibre 930 that guides emitted light rays 932 from the light source 912 to the dental tissue of the tooth 940. The optical fibre 930 also guides reflected scattered light rays 934 from the dental tissue of the tooth 940 to the spectrometer 914.

The processor 920 is configured to obtain the spectra of the detected scattered light; to obtain a spectral analysis result from the spectra and to determine a distance of the probe 910 to the pulp 944 of the tooth 940 based on the spectral analysis result. It should be noted that spectra equate to intensities of at least two optical wavelengths and the processor is configured to obtain the spectra of the detected scattered light in the wavelength range of 300-800 nm. To obtain a spectral analysis result from the spectra, the intensity of the spectra is determined in the range of 300-800 nm, wherein determining intensity also comprises determining intensity as part of the spectra. Further, to obtain a spectral analysis result from the spectra, light absorption peaks are detected, wherein the light absorption peaks have a wavelength range characteristic to a wavelength range of absorption spectra of blood. The wavelength ranges of absorption spectra of blood are within 520-550 nm and 570-590 nm. An integration operation is then performed on the determined intensity of the spectra of the scattered light.

The processor 920 is configured to determine the distance of the probe 910 to the pulp 944 of the tooth 940 based on the spectral analysis result, which comprises information regarding the integrated amplitude of the spectra and the detection of light absorption peaks. If the integrated amplitude of the spectra exceeds a threshold value and no light absorption peaks are detected, the processor is configured to determine a distance of the probe 910 to the pulp 944 of the tooth 940 is in the range of 1-2 mm. If the integrated amplitude of the spectra is lower than the threshold value and light absorption peaks are detected, the processor is configured to determine a distance of the probe 910 to the pulp 944 of the tooth 940 is in the range of 0.2-1 mm. If the integrated amplitude of the spectra is lower than the threshold value and light absorption peaks are not detected, the processor is configured to determine a distance of the probe 910 to the pulp 944 of the tooth 940 is less than 0.2 mm. The processor 920 is configured to measure the distance to the pulp 944 through the dentine 942 in real time. Hence, it gives warning mechanisms to the doctor when a certain distance to the pulp 944 is reached.

Figure 10:
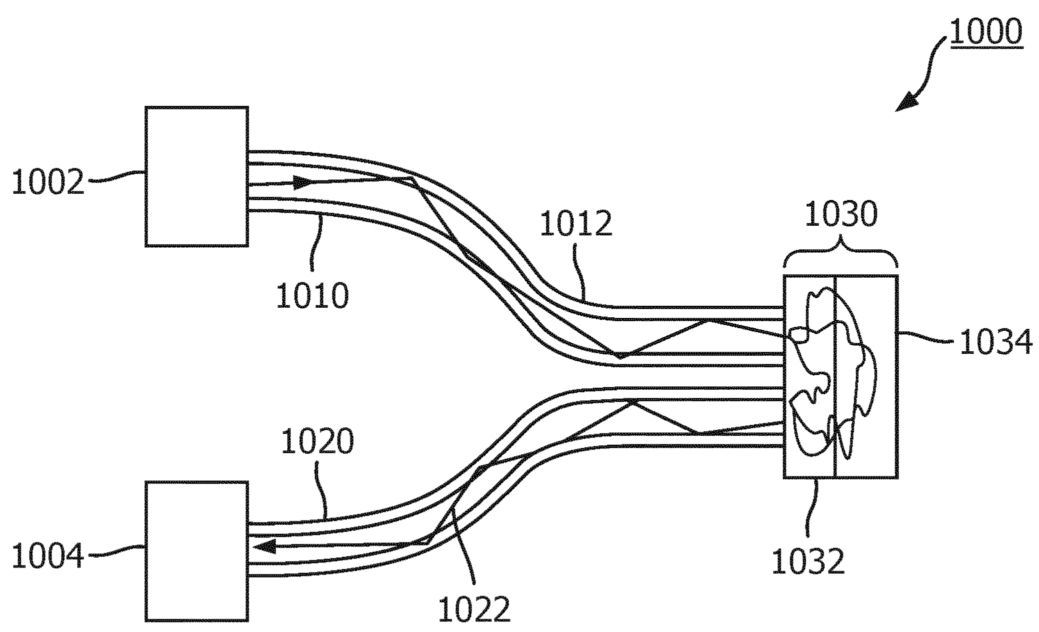
FIG. 10 shows a proposed probe embodiment comprising two optical fibres.

FIG. 10 shows a probe embodiment 1000 comprising two optical fibres 1010, 1020 that guide light rays to/from the dental tissue 1030, which comprises dentine 1032 and pulp 1034. The probe embodiment 1000 also comprises a light source 1002 and a spectrometer 1004. The optical fibre 1010 guides the emitted light ray 1012 from the light source 1002 to the dental tissue 1030. The optical fibre 1020 guides the reflected scattered light ray 1022 from the dental tissue 1030 to the spectrometer 1004.

Figure 11:
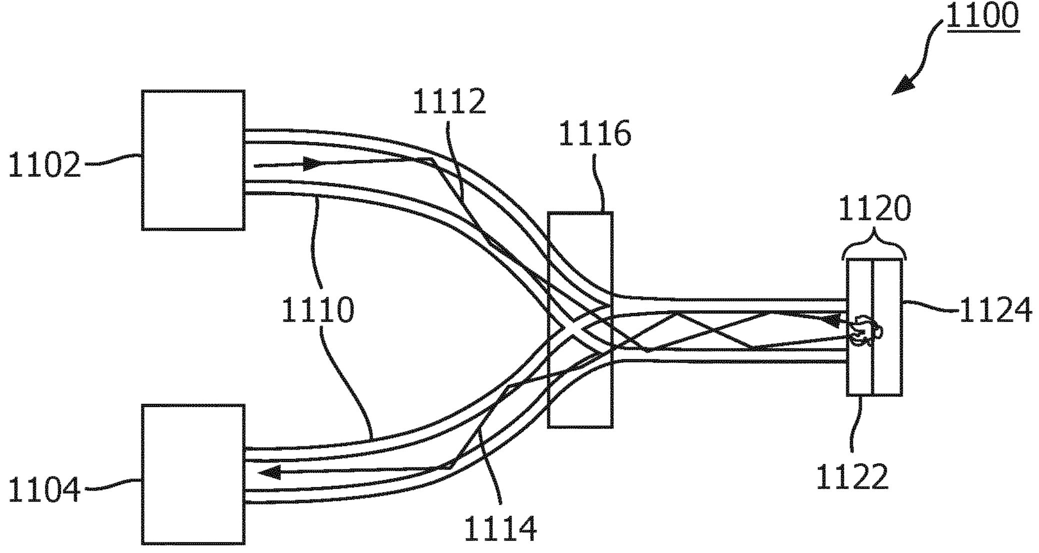
FIG. 11 shows a proposed probe embodiment comprising an optical fibre and a beamsplitter.

FIG. 11 shows a probe embodiment 1100 comprising an optical fibre 1110 and a beamsplitter 1116, wherein the optical fibre guides light rays to/from the dental tissue 1120, which comprises dentine 1122 and pulp 1124. The probe embodiment 1100 also comprises a light source 1102 and a spectrometer 1104. The optical fibre 1110 guides the emitted light ray 1112 from the light source 1102 to the dental tissue 1120. When used in conjunction with the beamsplitter 1116, the optical fibre 1110 also guides the reflected scattered light ray 1114 from the dental tissue 1120 to the spectrometer 1104.

Figure 12:
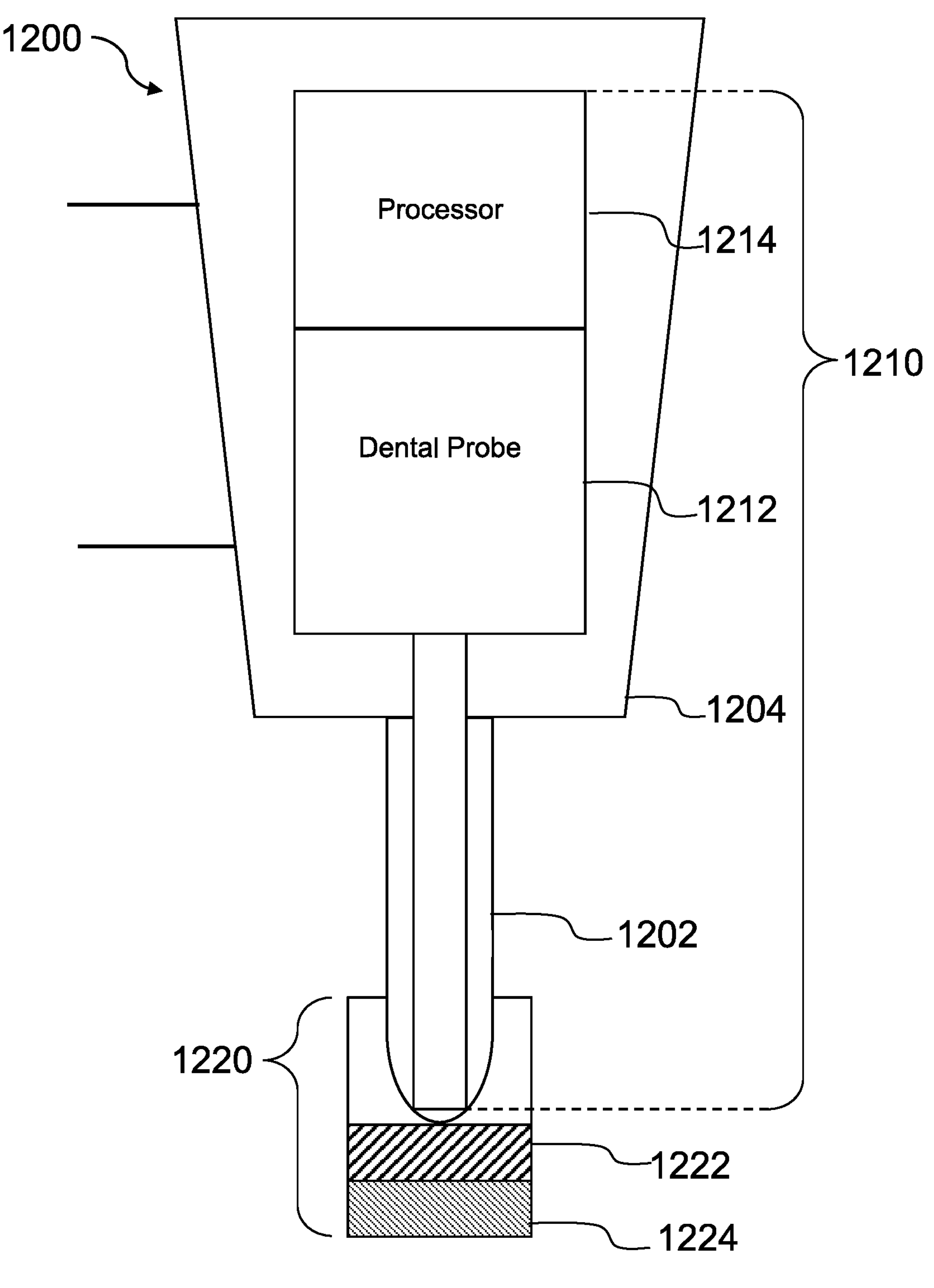
FIG. 12 shows a drill embodiment comprising a dental apparatus.

FIG. 12 shows a drill embodiment 1200 comprising a dental apparatus 1210. The drill embodiment comprises a drill bit 1202 affixed to a drill head 1204. In use, the curved distal end of the drill bit 1202 is positioned in close proximity to the dental tissue of the tooth 1220, which comprises dentine 1222 and pulp 1224. The dental apparatus 1210 comprises a dental probe 1212 and a processor 1214. The drill bit 1202 is large enough to accommodate optical fibres, hence the distal end of the dental probe 1212 is situated within the drill bit 1202. Therefore, the dental probe 1212 is also in close proximity to the dental tissue of the tooth 1220 and is configured to illuminate the dental tissue with light and to detect scattered light from the dental tissue. The light comprises having a wavelength range of 300-800 nm and comprises at least two different colors.

The processor 1214 is configured to obtain the spectra of the detected scattered light; to obtain a spectral analysis result from the spectra and to determine a distance of the probe 1212 to the pulp 1224 of the tooth 1220 based on the spectral analysis result. It should be noted that spectra equate to intensities of at least two optical wavelengths. The processor 1214 is configured to obtain the spectra of the detected scattered light in the wavelength range of 300-800 nm. To obtain a spectral analysis result from the spectra, the intensity of the spectra is determined in the range of 300-800 nm, wherein determining intensity also comprises determining intensity as part of the spectra. Further, to obtain a spectral analysis result from the spectra, light absorption peaks are detected, wherein the light absorption peaks have a wavelength range characteristic to a wavelength range of absorption spectra of blood. The wavelength ranges of absorption spectra of blood are within 520-550 nm and 570-590 nm.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality.

The mere fact that certain measures are recited in mutually different dependent claims does not indicate that a combination of these measures cannot be used to advantage. If the term "adapted to" is used in the claims or description, it is noted the term "adapted to" is intended to be equivalent to the term "configured to". Any reference signs in the claims should not be construed as limiting the scope.

The invention claimed is:

1. A method for detecting distance of a probe to pulp of a tooth by determining an indication of thickness of dentine of the tooth, comprising:

providing a probe having a light source and a spectrometer optically coupled to the probe, and a processor operatively coupled to the spectrometer;

receiving data representing scattered light from dental tissue illuminated by the light source of the probe, wherein the scattered light comprises light having a wavelength in the range of 300-800 nm;

obtaining spectra of the scattered light in a wavelength range of 300-800 nm by the spectrometer;

automatically detecting, by the processor executing a peak-detection algorithm, light absorption peaks in the spectra characteristic of blood;

computing, by the processor, an integrated amplitude of the spectra over a wavelength sub-range of 400-600 nm; and determining, by the processor, thickness of the dentine of the tooth based on (i) whether the integrated amplitude exceeds a predetermined threshold value and (ii) whether the light absorption peaks are detected in the range 400 nm to 600 nm, wherein:

when the integrated amplitude exceeds the predetermined threshold value and no light absorption peaks are detected, the thickness of the dentine is determined to be in the range of 2 mm to 1 mm;

when the integrated amplitude does not exceed the predetermined threshold value and light absorption peaks are detected, the thickness of the dentine is determined to be in the range 1 mm to 0.2 mm; and when the integrated amplitude does not exceed the predetermined threshold value and light absorption peaks are not detected, the thickness of the dentine is determined to be less than 0.2 mm; and outputting, by the processor, a shut-off signal to halt dental drilling when the determined thickness reaches a predetermined safety threshold.

2. The method according claim 1, wherein obtaining a spectral analysis result from the spectra comprises determining slopes of the intensities of the spectra in the range of 300-800 nm; and wherein the indication of thickness of the dentine of the tooth is determined using the determined slopes of intensities.

3. The method according to claim 1, wherein the wavelength range of light absorption spectra of blood is within 520-550 nm and 570-590 nm.

4. A dental apparatus for determining distance of a probe to pulp of a tooth by determining an indication of thickness of dentine of the tooth, comprising:

a probe configured to illuminate dental tissue of the tooth with light and to detect scattered light from the dental tissue, wherein the light comprises having a wavelength range of 300-800 nm;

a processor configured to:

obtain spectra of the detected scattered light in a wavelength range of 300-800 nm;

obtain a spectral analysis result from the spectra, wherein obtaining a spectral analysis result from the spectra comprises detecting light absorption peaks having a wavelength range characteristic to a wavelength range of absorption spectra of blood;

determine an indication of thickness of the dentine of the tooth based on the spectral analysis result; and determine that the thickness of the dentine is in the range of 2 mm to 1 mm, if the integrated amplitude of the spectra in the range 400 nm to 600 nm exceeds a predetermined threshold value and no light absorption peaks are detected in the range 400 nm to 600 nm, determine that the thickness of the dentine is in the range 1 mm to 0.2 mm, if the integrated amplitude of the spectra in the range 400 nm to 600 nm does not exceed the predetermined threshold value and light absorption peaks are detected in the range of 400 nm to 600 nm, and determine that the thickness of the dentine is less than 0.2 mm, if the integrated amplitude of the spectra in the range 400 nm to 600 nm does not exceed the predetermined threshold value and light absorption peaks are not detected in the range 400 nm to 600 nm.

5. The apparatus according to claim 4, wherein obtaining a spectral analysis result from the spectra comprises determining intensities of the spectra in the range of 300-800 nm.

6. The apparatus according to claim 4, wherein the wavelength ranges of absorption spectra of blood are within 520-550 nm and 570-590 nm.

7. The apparatus according to claim 4, wherein the probe is calibrated by measuring spectra of a reference portion of dentine.

* * * * *